(12) United States Patent
Constantine et al.

(10) Patent No.: US 10,925,825 B2
(45) Date of Patent: Feb. 23, 2021

(54) COMPOSITION

(71) Applicant: COSMETIC WARRIORS LIMITED, Poole (GB)

(72) Inventors: Margaret Joan Constantine, Poole (GB); Mark Constantine, Poole (GB); Helen Elizabeth Ambrosen, Wimborne (GB)

(73) Assignee: COSMETIC WARRIORS LIMITED, Poole (GB)

( * ) Notice: Subject to any disclaimer, the term of this patent is extended or adjusted under 35 U.S.C. 154(b) by 0 days.

(21) Appl. No.: 16/007,785

(22) Filed: Jun. 13, 2018

(65) Prior Publication Data

US 2018/0289608 A1 Oct. 11, 2018

Related U.S. Application Data

(63) Continuation of application No. 14/403,912, filed as application No. PCT/GB2013/051357 on May 23, 2013, now Pat. No. 10,022,316.

(30) Foreign Application Priority Data

May 25, 2012 (GB) .................................... 1209222

(51) Int. Cl.
| | | |
|---|---|---|
| *A61K 8/00* | (2006.01) | |
| *A61K 8/73* | (2006.01) | |
| *A61K 8/02* | (2006.01) | |
| *A61K 8/25* | (2006.01) | |
| *A61K 8/34* | (2006.01) | |
| *A61K 8/46* | (2006.01) | |
| *A61Q 19/10* | (2006.01) | |
| *A61Q 5/02* | (2006.01) | |

(52) U.S. Cl.
CPC ............ *A61K 8/732* (2013.01); *A61K 8/0216* (2013.01); *A61K 8/25* (2013.01); *A61K 8/345* (2013.01); *A61K 8/463* (2013.01); *A61Q 5/02* (2013.01); *A61Q 19/10* (2013.01); *A61K 2800/48* (2013.01)

(58) Field of Classification Search
None
See application file for complete search history.

(56) References Cited

U.S. PATENT DOCUMENTS

| | | | |
|---|---|---|---|
| 4,181,632 A | 1/1980 | Schebece | |
| 5,705,462 A | 1/1998 | Hormes et al. | |
| 5,801,134 A | 9/1998 | Righton | |
| 6,359,057 B1 | 3/2002 | Li | |
| 6,376,440 B1 * | 4/2002 | Hennen ................. | C11D 1/123 510/141 |
| 6,586,379 B1 | 7/2003 | Seipel | |
| 2007/0142257 A1 | 6/2007 | Hourigan | |
| 2007/0155639 A1 | 7/2007 | Salvador et al. | |
| 2011/0146534 A1 | 6/2011 | Uang | |
| 2011/0294711 A1 | 12/2011 | Brasilino de Carvalho et al. | |
| 2012/0053103 A1 * | 3/2012 | Sivik ..................... | C11D 17/06 510/218 |

FOREIGN PATENT DOCUMENTS

| | | |
|---|---|---|
| DE | 434312 A1 | 3/1996 |
| DE | 19708605 A1 | 9/1998 |
| DE | 10339807 A1 | 4/2005 |
| EP | 0186148 A2 | 7/1986 |
| EP | 0053970 B | 3/1992 |
| EP | 1150654 B1 | 9/2006 |
| GB | 2277325 A | 10/1994 |
| GB | 2346619 A | 8/2000 |
| GB | 2459093 A | 10/2009 |
| JP | S55-165998 A | 12/1980 |
| JP | H08-099819 A | 4/1996 |
| JP | H09-504316 A | 4/1997 |
| JP | H09-511248 A | 11/1997 |
| JP | 2000-038310 A | 2/2000 |
| JP | 2002-526643 A | 8/2002 |
| JP | 2006-513287 A | 4/2006 |
| KR | 1992-0002114 B1 | 3/1992 |
| OA | 09245 * | 6/1992 |
| OA | 09245 A | 6/1992 |
| RU | 95101032 | 3/1997 |
| WO | 95/026710 A1 | 10/1995 |
| WO | 98/39408 A1 | 9/1998 |
| WO | 00/47181 A1 | 8/2000 |
| WO | 01/59004 A1 | 8/2001 |
| WO | 2004/063320 A1 | 7/2004 |
| WO | 2006/138738 A1 | 12/2006 |
| WO | 2007/022229 A1 | 2/2007 |
| WO | 2010/003819 A1 | 1/2010 |
| WO | 2011/079163 A1 | 6/2011 |

(Continued)

OTHER PUBLICATIONS

Search Report for Japanese Patent Application No. 2015-513271, dated Jan. 31, 2017.
International Organization for Standardization, Representation of results of particle size analysis—Part 5: Methods of calculation relating to particle size analyses using logarithmic normal probability distribution, ISO 9276-5:2005.
Office Action for European Patent Application No. 13725451.2, dated Jan. 27, 2017.
Office Action dated Nov. 24, 2016 (Russian Patent Appln. No. 2014 152 474), english translation.
Office Action issued in corresponding Chinese Patent Application No. 201380027309.3, dated Jan. 11, 2016.

(Continued)

*Primary Examiner* — Necholus Ogden, Jr.
(74) *Attorney, Agent, or Firm* — Merchant & Gould P.C.

(57) ABSTRACT

The present invention provides a solid cosmetic composition comprising (i) corn starch in an amount of from about 20% to about 40%; (ii) bulking agent in an amount of from about 20% to about 50%; (iii) surfactant in an amount of from about 5% to about 30%; and (iv) glycerine in an amount of from about 15% to about 30%, present in an amount by weight of the total composition.

14 Claims, No Drawings

(56) References Cited

FOREIGN PATENT DOCUMENTS

| | | | |
|---|---|---|---|
| WO | WO-2011079163 A1 * | 6/2011 | ............. C11D 3/126 |
| WO | 2011/080101 A1 | 7/2011 | |
| WO | WO-2011080101 A1 * | 7/2011 | ............. C11D 9/007 |

OTHER PUBLICATIONS

International Search report and Written Opinion for International Application No. PCT/GB2012/051357 dated Jun. 23, 2014.
Office Action for Korean Patent Application No. 10-2014-7036229, dated Jul. 30, 2019.
Databank Mintel, "Tubby Putty Soap" Batman, Record-ID: 615254 (2006).
Recommended Use of "Tubby Putty Soap" Batman (enlarged page of Record-ID 615254) (2006).
Databank Mintel, "Snow Man Mouldable Soap" Oriflame, Record-ID 634283 (2006).
Notice of Opposition for European Patent Application No. 13725451.2, dated Nov. 28, 2019.

* cited by examiner

COMPOSITION

This application is a Continuation of U.S. patent application Ser. No. 14/403,912, filed 25 Nov. 2014, which is a National Stage Application of PCT/GB2013/051357, filed 23 May 2013, which claims benefit of Serial No. 1209222.7, filed 25 May 2012 in Great Britain and which applications are incorporated herein by reference. To the extent appropriate, a claim of priority is made to each of the above disclosed applications.

FIELD OF THE INVENTION

The present invention relates to a solid product for use as a cosmetic, a process for producing said product, and a product prepared by the method.

BACKGROUND TO THE INVENTION

The present invention relates to products particularly those for use in contact with the human body.

Surfactant products such as bubble baths, shampoos, shower gels and toothpastes are extremely well known cosmetic products and personal care products. These surfactant containing products are typically provided in the form of liquid or pastes. They are sold in containers to the end user and may be dispensed by the end user. However, the required use of packaging is a disadvantage. From an environmental perspective, waste packaging is a significant problem, despite the availability of recycling.

There is also a desire to provide more 'exciting' products which add to the bathing experience of a user. In other words, there is a desire to provide products which offer to the user more than the functional delivery of a surfactant to be able to wash the hair or skin as desired. In particular, the market in bathing products which offer some interaction or entertainment, particularly for children, has grown dramatically in recent years.

In many products, there is a requirement for mild formulations for the skin and hair, which whilst required for adults, also meets the need of children. In particular washing children's hair in the bath can be a difficult process. But providing a product they can play with as well as wash with, is a desirable outcome.

The present invention seeks to provide a solid cosmetic product which can be played with as well as washed with.

SUMMARY OF THE INVENTION

In a first aspect, there is provided a solid cosmetic composition comprising
(i) corn starch in an amount of from about 20% to about 40%;
(ii) bulking agent in an amount of from about 20% to about 50%;
(iii) surfactant in an amount of from about 5% to about 30%; and
(iv) glycerine in an amount of from about 15% to about 30%, present in an amount by weight of the total composition.

In a second aspect, there is provided a process for the production of a solid cosmetic composition comprising (i) corn starch; (ii) a bulking agent; (iii) a surfactant; and (iv) glycerine, the process comprising the steps of:
a) mixing
(i) corn starch in an amount of from about 20% to about 40%;
(ii) bulking agent in an amount of from about 20% to about 50%;
(iii) surfactant in an amount of from about 5% to about 30%; and
(iv) glycerine in an amount of from about 15% to about 30%, each present in an amount by weight of the total composition;
b) forming the mixture of step a) into a predetermined shape.

In a third aspect, there is provided a product obtained or obtainable by a process for the production of a solid cosmetic composition comprising
(i) corn starch in an amount of from about 20% to about 40%;
(ii) bulking agent in an amount of from about 20% to about 50%;
(iii) surfactant in an amount of from about 5% to about 30%; and
(iv) glycerine in an amount of from about 15% to about 30%, present in an amount by weight of the total composition.
the process comprising the steps of:
a) mixing
(i) corn starch in an amount of from about 20% to about 40%;
(ii) bulking agent in an amount of from about 20% to about 50%;
(iii) surfactant in an amount of from about 5% to about 30%; and
(iv) glycerine in an amount of from about 15% to about 30%,
each present in an amount by weight of the total composition;
b) forming the mixture of step a) into a predetermined shape.

For ease of reference, these and further aspects of the present invention are now discussed under appropriate section headings. However, the teachings under each section are not necessarily limited to each particular section.

Advantages

We have found that by providing a solid cosmetic composition comprising the specific components of the present invention, namely (i) corn starch in an amount of from about 20% to about 40%; (ii) bulking agent in an amount of from about 20% to about 50%; (iii) surfactant in an amount of from about 5% to about 30%; and (iv) glycerine in an amount of from about 15% to about 30%, present in an amount by weight of the total composition, we form a soft and putty like dough which is mouldable. It can be pushed and formed in to different shapes. A large bar of the composition in accordance with the present invention can be provided and pieces are then cut or pulled from the larger bar. They can be pressed in to different shapes and these then are used to wash with.

A suitable size piece of the present composition, for example a smaller piece pulled from a larger bar, is dampened with water and massaged on to the body to clean the skin. It is rinsed away with water, leaving the skin clean and soft. The mixture can also be applied to the hair by massaging a few times over the scalp to encourage a lather, then massaged further in to the hair and rinsed away to leave the hair clean. Any amount of the mixture left over can, if desired, be left on the side of the bath or in a shower to be used later. The mixture does not need a bottle or container to protect it as the form is that of a dough like solid.

The present composition has the ability to stay soft in texture when left un-wrapped. This quality was surprising. The composition does not require a rigid container, such as a plastic bottle or pot, because the product had the consistency of a dough. Therefore the conventional packaging required for a liquid product is not needed. The invention does not require any form of wrapping such as cellophane to protect it from an environment, which may be dusty such as in shop or store when it is being retailed. However, such a covering may be provided, if required.

The present composition is provided from a blend of well-known and cosmetically acceptable ingredients. The present composition does not require the presence of un-desirable ingredients, such as cosmetic preservatives. It is a dough like solid which may have a minimal water content, and which consequently does not require preservation in the way that high water content products do.

By addition of optional colours and fragrances, the present invention provides a dough like product which is colourful, fragrant and mouldable. This product is extremely desirable for children.

DETAILED DESCRIPTION

Composition

As discussed herein, in one aspect of the present invention, there is provided a solid cosmetic composition comprising (i) corn starch in an amount of from about 20% to about 40%; (ii) bulking agent in an amount of from about 20% to about 50%; (iii) surfactant in an amount of from about 5% to about 30%; and (iv) glycerine in an amount of from about 15% to about 30%, present in an amount by weight of the total composition.

The solid products of the present invention are compositions which can substantially sustain their physical shape when unsupported by external means, e.g. packaging etc. Thus, they are considered to be solid, solid like, in solid form or in solid-like form at room temperature. For the avoidance of doubt the solid product must remain substantially solid at up to 30° C.

By solid-like, it is understood that some materials are considered on a day to day basis to be solid, yet over an extremely long period of time, may alter in shape, e.g. amorphous materials such as glass etc. However, they are considered to be solid-like as, for the purpose they fulfil, they are solid.

Due to the solid form of the compositions of the present invention, external packaging is not required to maintain the shape of the composition.

Corn Starch

As discussed herein, the present composition, process, use and method, utilise corn starch. The term 'corn starch' used herein refers to the starch of corn (also known as maize) [*Zea mays*] grain and is obtained from the endosperm of the corn kernel. Corn starch is also known in some countries as corn flour or maize starch. Corn starch is not to be confused with cornmeal. Cornmeal is a coarse flour ground from dried maize or corn. In the United Kingdom corn starch is known as corn flour. Corn starch has mainly been used in foods, where it is used as a thickener for sauces and custards. In cosmetics it has been mainly used in talcum powders for babies.

Without being bound by theory, it is understood that the present composition provides it desirable dough like form based on the principle of using gels and mucilage to form a base, in to which the bulking agent (such as talc) and a surfactant is dispersed to form the dough. Glycerine is added to prevent the mixture from drying and becoming hard and non mouldable. Glycerine does not desiccate as water would, if used in the formulation, and so the presence of glycerine ensures the composition has a dough like soft texture.

Gels or mucilages are dispersions of ingredients, generally with water, which provide gel-like textures. They are often used in cosmetic products. Water, an essential ingredient for the skin, is held in suspension by the other ingredients. Gels and mucilages can be created, by using various ingredients. Seaweeds such as agar or carrageen, cellulose from synthetic cellulose such as hydroxyethylcellulose or clays such as bentonite, give robust gel like mixtures. Herbs such as marsh mallow (*Althea officinalis*) or flax (*Linum usitatissimum*) give moisture retentive mucilage. Gels produced in this way are very compatible with the skin and soften and moisturise it. The herbs mentioned, in particular, have been used for centuries to benefit the skin because of their mucilagenous properties.

The use of mucilages is advantageous in cosmetics where their moisturising quality helps the skin. Mild and effective, they are a type of ingredient that can be used in products for children and their mildness has been exploited for the basis of the present invention.

Corn starch with its long history of safe use in cosmetics and food provides an excellent base to make a solid form to carry surfactant which will cleanse the skin and the hair. The mucilaginous, thickening effect it provides carries the other ingredients within the composition. Its mildness and the ability to help the skin absorb moisture are also key features. Without being bound by theory, it is understood that the present composition provides a mucilage obtained from corn starch—this system provides a high quality means for binding other ingredients. In use, in contact with water the corn starch of the present composition is diluted and gives a milky solution, which softens the skin.

It will be appreciated by one skilled in the art that the corn starch is present in an amount of from about 20% to about 40% by weight of the total composition and is present in an amount to provide the desired solid cosmetic composition. In one aspect the corn starch is present in an amount of from about 25% to about 40%, such as an amount of from about 30% to about 40%, such as an amount of from about 30% to about 35%, such as an amount of approximately 32% by weight of the total composition.

Bulking Agent

As discussed herein, the present composition, process, use and method, utilise a bulking agent. As would be understood by one skilled in the art, the term 'bulking agent' used herein refers to a material which is solid and contributes to the mass and form of the solid cosmetic composition of the present invention. Typically the bulking agent will be a particulate material. For example the bulking agent may be an inert particulate material. In one aspect the bulking agent may be insoluble in water. In further aspects the bulking agent may be an insoluble particulate material. Yet further the bulking agent may be an insoluble inert material. Preferred bulking agents for use in the present invention are inert particulate insoluble materials.

As would be appreciated by one skilled in the art by the term "inert" it is meant a material which is not cosmetically active.

As would be appreciated by one skilled in the art by the term "particulate" it is meant a material which is predominantly made up of particles.

By the term "insoluble" it is meant that the material has a solubility in water at 35° C. of less than 1 g/100 mL, such as less than 0.5 g/100 mL, such as less than 0.1 g/100 mL, such as less than 0.05 g/100 mL, such as less than 0.02 g/100 mL.

The bulking agent, such as the talc, within the formulation, gives solidity to the form of the product. It should be inert and not irritating.

It will be appreciated by one skilled in the art that the bulking agent is present in an amount of from about 20% to about 50% by weight of the total composition and is present in an amount to provide the desired solid cosmetic composition. In one aspect the bulking agent is present in an amount of from about 20% to about 40%, such as an amount of from about 25% to about 40%, such as an amount of from about 30% to about 40%, such as an amount of from about 30% to about 35%, such as an amount of approximately 32% by weight of the total composition.

It is desirable that the bulking agent (such as an inert particulate bulking agent) does not impart a coarseness to the cosmetic composition of the present invention. If the particle size of the bulking agent (such as an inert particulate bulking agent) were too great, a less desirable feeling would be experienced by the user when applying the product to their skin or hair. In one aspect the bulking agent (such as an inert particulate bulking agent) has an average particle size of no greater than 5 µm, such as no greater than 4 µm, such as no greater than 3 µm, such as no greater than 2 µm, such as no greater than 1 µm. The average particle size may be measured in accordance with ISO Standard 9276-5 (Representation of results of particle size analysis).

In one preferred aspect the bulking agent is a clay. In one further aspect the bulking agent is selected from cosmetically acceptable salts, minerals, clays, titanium dioxide and mixtures thereof.

In one highly preferred aspect the bulking agent is selected from talc, kaolin, calamine, magnesium carbonate and mixtures thereof. Preferably the bulking agent is talc. Thus the present invention may further provide a solid cosmetic composition comprising (i) corn starch; (ii) talc (iii) a surfactant; and (iv) glycerine.

It will be appreciated by one skilled in the art that the talc may be present in an amount of from about 20% to about 50% by weight of the total composition and is present in an amount to provide the desired solid cosmetic composition. In one aspect the talc is present in an amount of from about 20% to about 40%, such as an amount of from about 25% to about 40%, such as an amount of from about 30% to about 40%, such as an amount of from about 30% to about 35%, such as an amount of approximately 32% by weight of the total composition.

Surfactant

The solid cosmetic product of the present invention comprises a surfactant. The surfactant is primarily selected from those surfactants known in the art to be suitable for application to the skin or hair. In one embodiment, the surfactant is selected from the group consisting of sodium laureth sulfate, sodium lauryl sulfate cocamide diethanolamine, lauryl betaine, sodium lauroyl sarcosinate, and mixtures thereof. In one embodiment, the surfactant is sodium laureth sulfate. Thus the present invention may further provide a solid cosmetic composition comprising (i) corn starch; (ii) bulking agent (iii) sodium laureth sulfate; and (iv) glycerine. The present invention may yet further provide a solid cosmetic composition comprising (i) corn starch; (ii) talc; (iii) sodium laureth sulfate; and (iv) glycerine.

In one aspect the surfactant used may be sodium laureth sulphate as it provides an effective cleansing action for the skin and the hair. It may be combined with other surfactants, for example sodium lauroyl sarcosinate. This blend with sodium laureth sulphate provides extra mildness and less potential for irritation, if required. Thus in one embodiment, the surfactant is selected from the group consisting of sodium laureth sulfate, sodium lauroyl sarcosinate, and mixtures thereof. In one embodiment, the surfactant is sodium laureth sulphate and sodium lauroyl sarcosinate.

It will be appreciated by one skilled in the art that the surfactant is present in an amount of from about 5% to about 30% by weight of the total composition and is present in an amount to provide the desired solid cosmetic composition. In one embodiment, the surfactant is present in an amount of from about 5% to about 25%, such as in an amount of from about 5% to about 20%, such as in an amount of from about 5% to about 15%, such as in an amount of from about 5% to about 10%, such as in an amount of approximately 8% by weight of the total composition.

The surfactant of the solid cosmetic composition provides the composition with the ability to achieve its required purpose. Thus for a shampoo, the surfactant removes dirt and grease from the user's hair. Thus for a body soap, the surfactant removes dirt and grease from the user's skin.

In one embodiment, the surfactant product is a shampoo. In one embodiment, the surfactant product is a shower gel. In one embodiment, the surfactant product is a facial wash. In one embodiment, the surfactant product is a bubble bath.

Glycerine

The surfactant product of the present invention also comprises glycerine. Glycerine is also known as glycerine, glycerol and propane-1,2,3-triol.

Glycerine is an essential ingredient of the composition of the present invention. Glycerine is known to be mild and has a long history of safe use within cosmetics. Glycerine is a humectant, which is a descriptive term for its ability to help the skin to absorb water. The water mixed with the product during use is therefore able to benefit the skin and soften it further by the presence of glycerine. This ingredient further prevents the composition for drying and becoming hard and crumbly. The texture of the invention is protected by the presence of glycerine in the formula.

It will be appreciated by one skilled in the art that the glycerine is present in an amount of from about 15% to about 30% by weight of the total composition and is present in an amount to achieve the desired aims of the present invention. In one aspect glycerine is present in an amount of from about 20% to about 30%, such as from about 22% to about 28%, such as from about 24% to about 26%, such as approximately 25% based on the weight of the total composition.

Process

As discussed herein, the invention provides a process for the production of a solid cosmetic composition comprising (i) corn starch in an amount of from about 20% to about 40%; (ii) bulking agent in an amount of from about 20% to about 50%; (iii) surfactant in an amount of from about 5% to about 30%; and (iv) glycerine in an amount of from about 15% to about 30%, present in an amount by weight of the total composition, the process comprising the steps of: a) mixing (i) corn starch in an amount of from about 20% to about 40%; (ii) bulking agent in an amount of from about 20% to about 50%; (iii) surfactant in an amount of from about 5% to about 30%; and (iv) glycerine in an amount of from about 15% to about 30%, present in an amount by weight of the total composition. b) forming the mixture of step a) into a predetermined shape.

The shape of the solid products of the present invention is not limited. It may be that the solid products are provided with a shape which would be aesthetically pleasing and/or which aids in the use of the product. For example, it may be that the solid product is produced in such a manner so that it is formed in a shape which is ergonomically acceptable to the user. Therefore, in one embodiment of the process of the present invention, the mixture of step a) is pressed into a mould, and then turned out to produce the solid product. The product may also be formed into long shapes or rolls. For example, solid cosmetic composition in accordance with the present invention may be pushed through a die to form an extruded shape. Alternatively the product can be manipulated, for example by hand, into a roll. Sections may then be cut from the roll or the extruded product to provide an ergonomically acceptable shape slice for the end user.

As described herein, the solid product may further comprise one or more cosmetically acceptable additives. In one embodiment, the process further comprises the step of combining with the mixture of step a) one or more cosmetically acceptable additives as defined herein.

The present invention also provides a product obtained or obtainable by a process for the production of a solid cosmetic composition comprising (i) corn starch in an amount of from about 20% to about 40%; (ii) bulking agent in an amount of from about 20% to about 50%; (iii) surfactant in an amount of from about 5% to about 30%; and (iv) glycerine in an amount of from about 15% to about 30%, present in an amount by weight of the total composition, the process comprising the steps of: a) mixing (i) corn starch in an amount of from about 20% to about 40%; (ii) bulking agent in an amount of from about 20% to about 50%; (iii) surfactant in an amount of from about 5% to about 30%; and (iv) glycerine in an amount of from about 15% to about 30%, present in an amount by weight of the total composition, b) forming the mixture of step a) into a predetermined shape.

Preferred Compositions & Additional Components

The solid product of the present invention may also comprise one or more cosmetically acceptable additives. The person skilled in the art is aware of a range of cosmetically acceptable additives which are suitable for incorporation into such compositions. For example, binders, fillers, opacifiers, perfumes, colours, fragrances, decorative items and mixtures thereof. Preferably the solid cosmetic composition comprises at least one additional component selected from colours, fragrances and mixtures thereof.

The combined amount of cosmetically acceptable additives is preferably from about 0.1% to about 10% by weight of the total composition, such as from about 0.1% to about 5% by weight of the total composition, such as from about 0.5% to about 5% by weight of the total composition, such as from about 1% to about 5% by weight of the total composition, such as from about 1% to about 4% by weight of the total composition, such as from about 1% to about 3% by weight of the total composition, such as from about 1% to about 2% by weight of the total composition.

The combined amount of colours and fragrances is preferably from about 0.1% to about 10% by weight of the total composition, such as from about 0.1% to about 5% by weight of the total composition, such as from about 0.5% to about 5% by weight of the total composition, such as from about 1% to about 5% by weight of the total composition, such as from about 1% to about 4% by weight of the total composition, such as from about 1% to about 3% by weight of the total composition, such as from about 1% to about 2% by weight of the total composition.

Fruit and herb extracts and juices, vegetable oils and essential oils are all compatible with the composition. Colours, both naturally derived and synthetic can be used to colour the product. Cosmetic colour is added to the invention to form bright colourful shapes and bars of the mixture. This colour can be a blend of synthetic cosmetic pigments, such as FD&C Blue No 1, FD&C Red No 4 and others. Also naturally derived colours such as gardenia extract or chloropyl extract.

The amount of colour is preferably from about 0.01% to about 10% by weight of the total composition, such as from about 0.01% to about 5% by weight of the total composition, such as from about 0.01% to about 4% by weight of the total composition, such as from about 0.01% to about 3% by weight of the total composition, such as from about 0.01% to about 2% by weight of the total composition, such as from about 0.02% to about 2% by weight of the total composition, such as from about 0.05% to about 2% by weight of the total composition, such as from about 0.1% to about 2% by weight of the total composition, such as from about 0.2% to about 2% by weight of the total composition, such as from about 0.2% to about 1% by weight of the total composition, such as from about 0.2% to about 0.8% by weight of the total composition, such as from about 0.2% to about 0.6% by weight of the total composition, such as from about 0.4% to about 0.6% by weight of the total composition.

To discourage children from ingesting the composition, a bittering agent can be added to ensure that if the mixture is taken in to the mouth, that it will not be swallowed. Materials such as Bitrex or Denatonium Benzoate may be added (Bitrex is a registered trademark of Johnson Matthey-Macfarlan Smith of Edinburgh Scotland for the product denatonium benzoate.) Grapefruit seed extract, which is from the pulp of grapefruit, may also be added as it gives a bitter taste. Other agents of a similar action could be included.

The amount of bittering agent is preferably from about 0.005% to about 0.5% by weight of the total composition, such as from about 0.005% to about 0.4% by weight of the total composition, such as from about 0.005% to about 0.3% by weight of the total composition, such as from about 0.005% to about 0.2% by weight of the total composition, such as from about 0.005% to about 0.15% by weight of the total composition, such as from about 0.005% to about 0.1% by weight of the total composition, such as from about 0.01% to about 0.1% by weight of the total composition, such as from about 0.02% to about 0.1% by weight of the total composition, such as from about 0.03% to about 0.1% by weight of the total composition, such as from about 0.04% to about 0.1% by weight of the total composition, such as from about 0.04% to about 0.08% by weight of the total composition, such as from about 0.05% to about 0.07% by weight of the total composition.

In one embodiment, the cosmetically acceptable additives are selected from the group consisting of essential oils, vitamins, fragrances, colourings, clays, decorative articles and mixtures thereof.

Fragrance may be added to the product to make the experience of using the present composition more pleasant. combining essential oils such as lavender, chamomile or rose absolute into fragrances for the invention ensures the user has a pleasant washing experience.

The amount of fragrances is preferably from about 0.1% to about 10% by weight of the total composition, such as from about 0.1% to about 5% by weight of the total composition, such as from about 0.1% to about 4% by weight of the total composition, such as from about 0.5% to about 5% by weight of the total composition, such as from about 1% to about 5% by weight of the total composition, such as from about 0.5% to about 4% by weight of the total composition, such as from about 0.5% to about 3% by weight of the total composition, such as from about 0.5% to about 2% by weight of the total composition, such as from about 0.5% to about 1.5% by weight of the total composition.

The essential oils may be selected based on the fragrance desired, skin type to be treated and other effects desired based on the well-known properties of essential oils. The addition of essential oils, when taken in to the nose, are known to alter mood. For example, essential oils are known to create effects of drowsiness or stimulating the senses. Many well documented effects can be achieved by the use of essential oils.

In one embodiment, the one or more essential oils present in the solid product are selected from Tarragon, Lemon myrtle, Jasmin, Ylang ylang, Labdanum, Lemongrass, Rose otto, Grapefruit, Patchouli, Rosemary, Armois, Lemon, Neroli, Sweet violet, Lavender, Orange 50 fold, Vanilla, Peppermint, Benzoin, Hydrangia, Litsea Cubeba, Cardamon, Tonka, and Chamomile blue. In one embodiment, the one or more essential oils present in the solid product are selected from Tarragon, Lemon myrtle, Labdunum, and Lemon.

Vitamins, particularly B, C and E are very beneficial for the skin. Vitamin rich ingredients such as Wheatgerm oil can also be used to deliver vitamins on to the skin. In a one embodiment, the vitamins are selected from vitamin B, vitamin C, vitamin E and mixtures thereof. It will be appreciated by one skilled in the art that the vitamin may be provided from any suitable source. For example the vitamin(s) may be provided from a synthetic source or from incorporation into the solid product of a material, such as a natural material, that has a high vitamin content.

The ingredients of the present invention do not require cosmetic preservatives. The use of cosmetic preservatives can increase the potential to irritate the skin.

The above ranges provide preferred amounts of each of the components. Each of these ranges may be taken alone or combined with one or more other component ranges to provide a preferred aspect of the invention.

A highly preferred composition of the present invention or for use in the present invention is a solid cosmetic composition comprising
(i) corn starch in an amount of from about 20% to about 40%;
(ii) talc in an amount of from about 20% to about 50%;
(iii) surfactant in an amount of from about 5% to about 30%; and
(iv) glycerine in an amount of from about 15% to about 30%, present in an amount by weight of the total composition.

A highly preferred composition of the present invention or for use in the present invention is a solid cosmetic composition comprising
(i) corn starch in an amount of from about 20% to about 40%;
(ii) bulking agent in an amount of from about 20% to about 50%;
(iii) sodium laureth sulphate in an amount of from about 5% to about 30%; and
(iv) glycerine in an amount of from about 15% to about 30%, present in an amount by weight of the total composition.

A highly preferred composition of the present invention or for use in the present invention is a solid cosmetic composition comprising
(i) corn starch in an amount of from about 20% to about 40%;
(ii) talc in an amount of from about 20% to about 50%;
(iii) sodium laureth sulphate in an amount of from about 5% to about 30%; and
(iv) glycerine in an amount of from about 15% to about 30%, present in an amount by weight of the total composition.

Method

In one aspect of the present invention, there is provided a method comprising contacting the skin of a user with water in which the solid product as defined herein has dissolved or in which the solid product as defined herein is dissolving. In a typical method water in run in to the bath at acceptable temperature. The user immerses their body in the water and the solid product is immersed in the water. The user then washes their hair or body as described herein.

It can be seen from the description of the invention and it's properties that a mixture such as this will be fun and pleasurable, particularly for children. Having a dough like mixture to play with in the bath or shower which children can shape and mould, which can then be used to wash their skin and hair will be a great encouragement to wash as well as a fun experience at bath time.

Further Aspects

The present invention further provides broad aspects wherein the amounts of (i) corn starch; (ii) a bulking agent; (iii) a surfactant; and/or (iv) glycerine are not limited in the manner described herein.

In a first broad aspect, there is provided a solid cosmetic composition comprising
(i) corn starch;
(ii) a bulking agent;
(iii) a surfactant; and
(iv) glycerine.

In a second broad aspect, there is provided a process for the production of a solid cosmetic composition comprising (i) corn starch; (ii) a bulking agent; (iii) a surfactant; and (iv) glycerine, the process comprising the steps of:
a) mixing
(i) corn starch;
(ii) a bulking agent;
(iii) a surfactant; and
(iv) glycerine;
b) forming the mixture of step a) into a predetermined shape.

In a third broad aspect, there is provided a product obtained or obtainable by a process for the production of a solid cosmetic composition comprising (i) corn starch; (ii) a bulking agent; (iii) a surfactant; and (iv) glycerine, the process comprising the steps of:
a) mixing (i) corn starch; (ii) a bulking agent; (iii) a surfactant; and (iv) glycerine;
b) forming the mixture of step a) into a predetermined shape.

It will be appreciated by one skilled in the art that in each of the first broad aspect, the second broad aspect and the third broad aspect, the corn starch may be present in any suitable amount to provide the desired solid cosmetic composition. In each of the first broad aspect, the second broad aspect and the third broad aspect, the corn starch may be present in an amount of from about 5% to about 60%, such as in an amount of from about 10% to about 50%, such as an amount of from about 20% to about 40%, such as an amount of from about 25% to about 40%, such as an amount of from about 30% to about 40%, such as an amount of from about 30% to about 35%, such as an amount of approximately 32% by weight of the total composition.

It will be appreciated by one skilled in the art that in each of the first broad aspect, the second broad aspect and the third broad aspect, the bulking agent may be present in any suitable amount to provide the desired solid cosmetic composition. In each of the first broad aspect, the second broad aspect and the third broad aspect, the bulking agent may be present in an amount of from about 5% to about 60%, such as in an amount of from about 10% to about 50%, such as an amount of from about 20% to about 50%, such as an amount of from about 20% to about 40%, such as an amount of from about 25% to about 40%, such as an amount of from about 30% to about 40%, such as an amount of from about 30% to about 35%, such as an amount of approximately 32% by weight of the total composition.

It will be appreciated by one skilled in the art that in each of the first broad aspect, the second broad aspect and the third broad aspect, the surfactant may be present in any suitable amount to provide the desired solid cosmetic composition. In each of the first broad aspect, the second broad aspect and the third broad aspect, the surfactant may be present in an amount of from about 5% to about 50% such as in an amount of from about 5% to about 40%, such as in an amount of from about 5% to about 30%, such as in an amount of from about 5% to about 25%, such as in an amount of from about 5% to about 20%, such as in an amount of from about 5% to about 15%, such as in an amount of from about 5% to about 10%, such as in an amount of approximately 8% by weight of the total composition. In one embodiment, the surfactant, or the mixture of surfactants, is present in an amount of from about 5% to about 30% by weight of the total composition.

It will be appreciated by one skilled in the art that in each of the first broad aspect, the second broad aspect and the third broad aspect, the glycerine may be present in any suitable amount to provide the desired solid cosmetic composition. In each of the first broad aspect, the second broad aspect and the third broad aspect, the glycerine may be present in an amount of from about 5% to about 50%, such as from about 5% to about 40%, such as from about 10% to about 40%, such as from about 10% to about 35%, such as from about 10% to about 30%, such as from about 15% to about 30%, such as from about 20% to about 30%, such as from about 22% to about 28%, such as from about 24% to about 26%, such as approximately 25% based on the weight of the total composition.

Each of the amounts of (i) corn starch (ii) bulking agent (iii) surfactant and (iv) glycerine recited herein in respect of the first broad aspect, the second broad aspect and the third broad aspect, may be combined to preferred compositions. For example the composition may contain (i) corn starch in an amount of from about 5% to about 60%;

(ii) bulking agent in an amount of from about 5% to about 60%;

(iii) surfactant in an amount of from about 5% to about 50%; and (iv) glycerine in an amount of from about 5% to about 50%, by weight of the total composition.

EXAMPLES

The invention will now be described with reference to the following non-limiting example.

A solid product having the following composition was prepared. The formula is as follows:

| | | Grams |
|---|---|---|
| | Batch Size: | 100.0 |
| Formula % | Raw Material Type | |
| 32.60 | Corn starch | 32.60 |
| 32.60 | Talc | 32.60 |
| 8.00 | Sodium laureth sulfate | 8.00 |
| 0.50 | Crocin extract (colour) | 0.50 |
| 25.24 | Glycerine | 25.24 |
| 0.06 | Bitrex | 0.06 |
| 1.00 | Fragrance | 1.00 |
| 100.00 | | 100.000 |

Method:
1. the sodium laureth sulphate is combined with the colour (Crocin extract) and blended.
2. the glycerine, Bitrex and fragrance is added to this.
3. the talc, then finally the corn starch is added to form a soft dough-like texture.
4. the mix is then left to settle for thirty minutes. Then it is finally moulded or shaped into rolls.

The final product is used in a bath or shower. The user breaks from the larger mass of product enough material for a single use. The product is rubbed between the hands to form lather. The lather is then applied to the hair and to the body to wash both.

Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

The invention claimed is:

1. A solid cosmetic composition comprising
   (i) corn starch in an amount of from about 20% to about 40%;
   (ii) bulking agent in an amount of from about 20% to about 50%, wherein the bulking agent is selected from the group consisting of a clay, talc, titanium dioxide, and mixtures thereof;
   (iii) surfactant in an amount of from about 5% to about 30%, wherein the surfactant is sodium laureth sulfate; and
   (iv) glycerine in an amount of from about 15% to about 30%,
   present in an amount by weight of the total composition.

2. A solid cosmetic composition according to claim 1, wherein the corn starch is present in an amount of from about 25% to about 40% by weight of the total composition.

3. A solid cosmetic composition according to claim 1 or 2, wherein the bulking agent is present in an amount of from about 20% to about 40% by weight of the total composition.

4. A solid cosmetic composition according to claim 1, 2 or 3, wherein the surfactant is present in an amount of from about 5% to about 25% by weight of the total composition.

5. A solid cosmetic composition according to any one of the preceding claims, wherein the glycerine is present in an amount of from about 20% to about 30% by weight of the total composition.

6. A solid cosmetic composition according to claim 1 comprising
   (i) corn starch in an amount of from about 25% to about 40%;
   (ii) bulking agent in an amount of from about 40% to about 50%;
   (iii) surfactant in an amount of from about 5% to about 25%; and
   (iv) glycerine in an amount of from about 20% to about 30%,
   present in an amount by weight of the total composition.

7. A solid cosmetic composition according to any one of the preceding claims, wherein the clay is selected from the group consisting of kaolin, calamine and mixtures thereof.

8. A solid cosmetic composition according to any one of the preceding claim 1, 2, 3, 4, 5 or 6, wherein the bulking agent is talc.

9. A solid cosmetic composition according to any one of the preceding claims, further comprising at least one additional component selected from binders, fillers, opacifiers, perfumes, colours, fragrances, decorative items and mixtures thereof.

10. A solid cosmetic composition according to claim 9, further comprising at least one additional component selected from colours, fragrances and mixtures thereof.

11. A solid cosmetic composition according to claim 10, wherein the combined amount of colours and fragrances is from about 1% to about 5% by weight of the total composition.

12. A process for the production of a solid cosmetic composition as defined in claim 1 comprising the steps of:
   a) mixing
      (i) corn starch in an amount of from about 20% to about 40%;
      (ii) bulking agent in an amount of from about 20% to about 50%, wherein the bulking agent is selected from the group consisting of a clay, titanium dioxide, and mixtures thereof;
      (iii) surfactant in an amount of from about 5% to about 30%, wherein the surfactant is sodium laureth sulfate; and
      (iv) glycerine in an amount of from about 15% to about 30%,
      each present in an amount by weight of the total composition,
   b) forming the mixture of step a) into a shape.

13. A product obtained or obtainable by the process of claim 12.

14. A cosmetic method comprising contacting the skin or hair of a user with water into which is dissolved a solid cosmetic composition as defined in claim 1.

* * * * *